US00PP27903P3

(12) United States Plant Patent
Jordan

(10) Patent No.: US PP27,903 P3
(45) Date of Patent: Apr. 18, 2017

(54) ARTICHOKE PLANT NAMED 'SJ215'

(50) Latin Name: *Cynara scolymus*
Varietal Denomination: SJ215

(71) Applicant: Steve Jordan, Lompoc, CA (US)

(72) Inventor: Steve Jordan, Lompoc, CA (US)

( * ) Notice: Subject to any disclaimer, the term of this patent is extended or adjusted under 35 U.S.C. 154(b) by 169 days.

(21) Appl. No.: 13/854,901

(22) Filed: Apr. 1, 2013

(65) Prior Publication Data

US 2014/0075622 P1 Mar. 13, 2014

(51) Int. Cl.
*A01H 5/02* (2006.01)

(52) U.S. Cl.
USPC ..... Plt./258
CPC ..... *A01H 5/025* (2013.01)

(58) Field of Classification Search
USPC ..... Plt./258
See application file for complete search history.

(56) References Cited

U.S. PATENT DOCUMENTS

PP21,593 P2 * 12/2010 Colfer ..... Plt./258

* cited by examiner

*Primary Examiner* — Susan McCormick Ewoldt
(74) *Attorney, Agent, or Firm* — Ballew Law

(57) ABSTRACT

A new cultivar of artichoke named 'SJ215' that is distinguishable by its upright habit and numerous tightly compact immature edible flower buds that are pale-violet in color. In combination these traits set 'SJ215' apart from all other existing cultivars of *Cynara scolymus* known to the inventor.

6 Drawing Sheets

Genus and species: *CYNARA scolymus.*
Variety denomination: 'SJ215'.

CROSS-REFERENCE TO RELATED APPLICATIONS

None

STATEMENT REGARDING FEDERALLY SPONSORED RESEARCH OR DEVELOPMENT

None

BACKGROUND AND SUMMARY OF THE VARIETY

The present invention relates to a new and distinct cultivar of artichoke plant known commonly as Globe artichoke a perennial herb that is grown as a food crop for the production of edible vegetable delicacies. The new invention is known botanically as *CYNARA scolymus* and will be referred to hereinafter by the cultivar name 'SJ215'. *Cynara* is in the family Asteraceae, formerly known as Compositae.

An individual plant of *Cynara scolymus* 'SJ215' is comprised of main stem, lateral stems, leaves, and immature flower buds known as involucre. Each involucrum is made up of imbricate phyllaries also known as involucral bracts. Freshly harvested immature flower buds can be baked, grilled, boiled, or steamed, making the fleshy part of the bracts, the fleshy receptacle, and the uppermost part of the peduncle, edible. If not harvested, but permitted to mature, flower buds will develop into flower heads known as capitula.

The new *Cynara* variety named 'SJ215' was discovered as a natural somaclonal variant (sport) derived in a commercial crop in Lompoc, Calif. from the following parent: An individual *Cynara scolymus* 'BCL 9-11' (U.S. Plant Pat. No. 15,807).

The inventor selected the new cultivar named 'SJ 215' based on the criterion of immature flower bud color. The new cultivar named 'SJ 215' was discovered in and amongst a commercially grown crop of *Cynara scolymus* 'BCL 9-11' in Lompoc, Calif. The new cultivar was a limb sport mutation from the 'BCL 9-11' parent plant. At the time of discovery 'SJ 215' was segregated and labeled for observation. No chemicals or other methods, known to the inventor, were used to induce the new cultivar named 'SJ 215'.

The closest comparison plant is *Cynara scolymus* 'BVC 8-11' (PP 164299'BCL 9-11' (U.S. Plant Pat. No. 15,807). The color of the edible immature flower buds of *Cynara scolymus* 'SJ215' is red. By comparison, the color of the edible immature flower buds of the parent *Cynara scolymus* 'BCL 9-11' (U.S. Plant Pat. No. 15,807) is green.

The new *Cynara scolymus* cultivar named 'SJ 215' is characterized by upright habit, green leaves and stems, and numerous tightly compact immature flower buds that are pale-violet in color. Propagation of the new cultivar named 'SJ 215' is accomplished using vegetative cuttings and tissue culture. Cultural requirements include full sun, well-draining alluvial soil, and moderate water. Hardiness is classified as USDA Zone 6.

The first asexual propagation of the new cultivar named 'SJ 215', was conducted by the inventor in March 2010, using the method of vegetative cuttings. Asexual propagation was conducted in Lompoc, Calif. From these cuttings resulted 151 rooted cuttings. The 151 rooted cuttings were grown out and from the grown plants vegetative cuttings were taken resulting in 768 rooted cuttings. The 768 rooted cuttings were grown out and from the grown plants vegetative cuttings were taken, resulting in 1000 rooted cuttings, which then served as explant material for subsequent asexual propagation by tissue culture in April 2011. Since 2010 under careful observation the new *Cynara scolymus* cultivar named 'SJ 215' is determined uniform, stable and true to type in subsequent generations of asexual propagation.

SUMMARY OF THE INVENTION

The following traits have been repeatedly observed and represent the distinguishing characteristics of the new *Cynara* cultivar named 'SJ215'. These traits in combination distinguish 'SJ215' from all other existing varieties of *Cynara* known to the inventor. 'SJ215' has not been tested under all possible conditions and phenotypic differences may be observed with variations in environmental, climatic, and cultural conditions, however, without any variance in genotype.

1. 'SJ 215' exhibits upright habit.
2. The immature flower buds of 'SJ 215' are pale-violet in color.
3. The immature flower buds of 'SJ 215' are tightly compact.
4. 'SJ 215' is asexually propagated using the method of vegetative cuttings and tissue culture.
5. 'SJ 215' grows in full sun and well-draining alluvial soil, with moderate water.
6. 'SJ 215' is hardy to USDA Zone 6.

BRIEF DESCRIPTION OF THE DRAWINGS

The accompanying color drawings illustrate the overall appearance of the new *Cynara* cultivar named 'SJ215' showing color as true as is reasonably possible to obtain in color reproductions of this type. Color in the drawings may differ from color values cited in the detailed botanical description, which accurately describe the actual color of the new variety 'SJ215'.

Drawings were made in March 2012 of field grown plants in Lompoc, Calif. Lompoc is located on California's central coast in Santa Barbara County. Conditions can vary with air temperatures ranging from 15.5° Centigrade to 26.6° Centigrade. The relative humidity is generally high. Prevailing winds are northwesterly and rainfall averages 30.48 cm. per year. The plants depicted in the accompanying drawings were two years old at the time the drawings were prepared.

Figure 1:
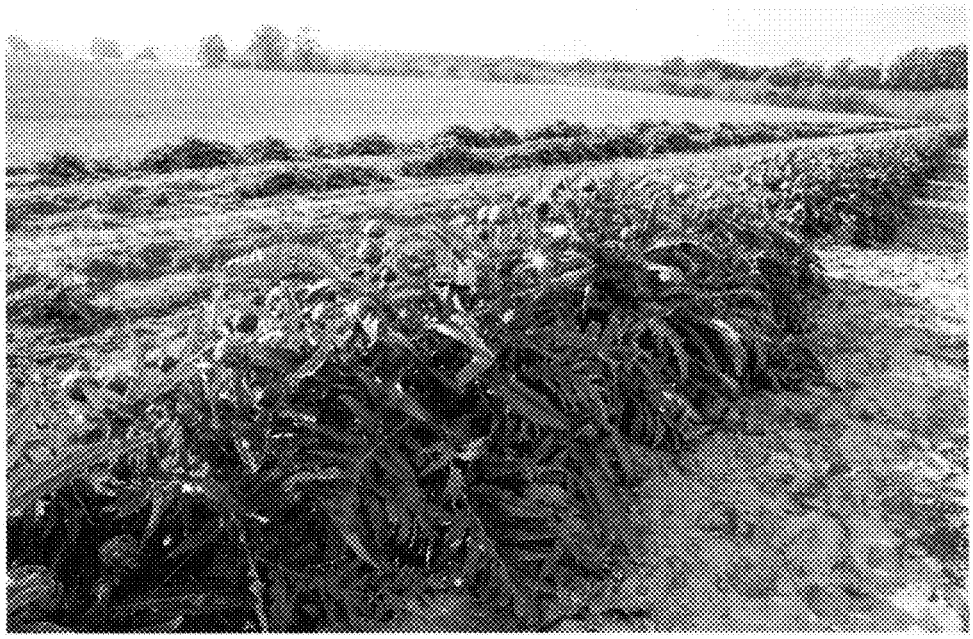
FIG. 1 depicts field grown plants of 'SJ 215' in Lompoc, Calif.
Figure 2:
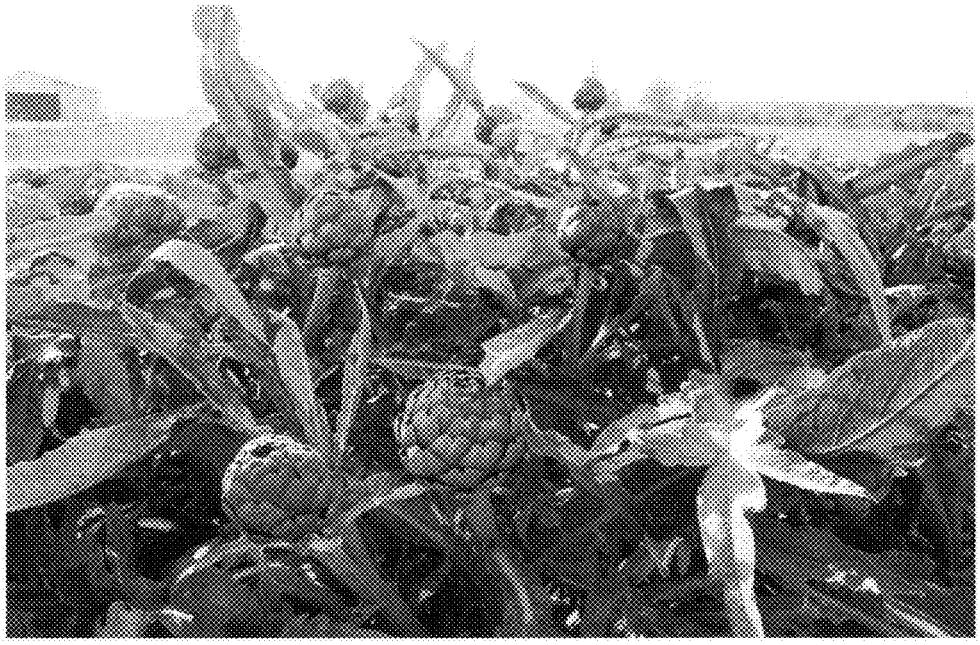
FIG. 2 depicts a close image of the immature flower buds on field grown plants in Lompoc, Calif.
Figure 3:
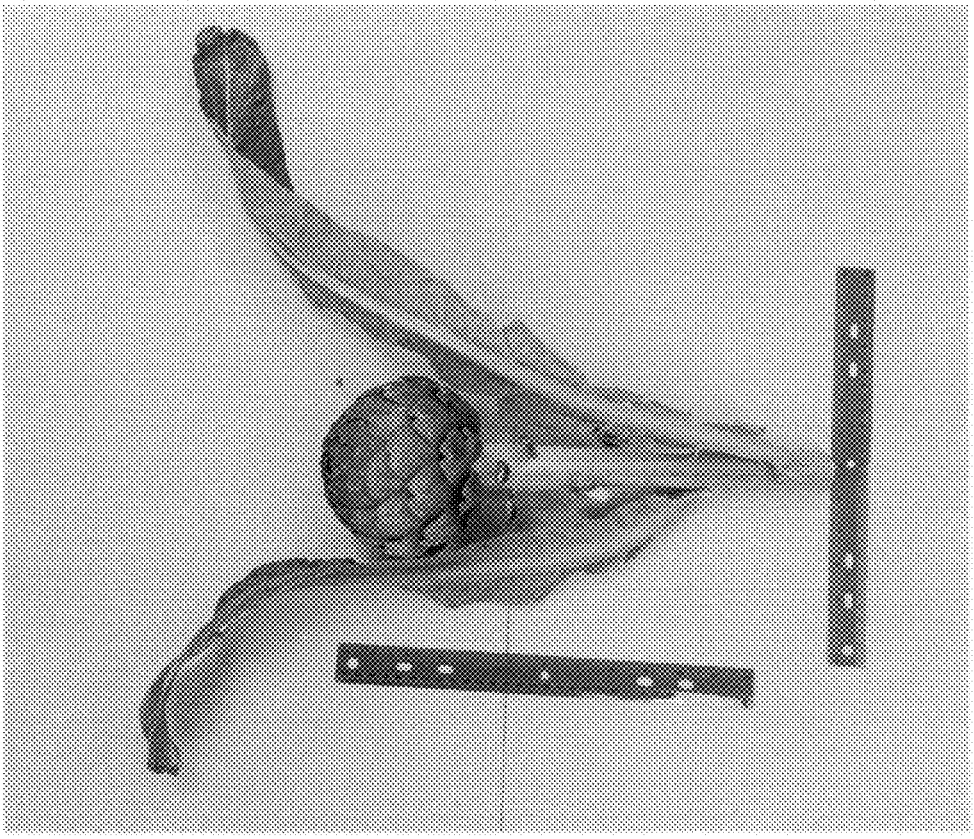
FIG. 3 depicts a harvested pale-violet immature flower bud on peduncle with leaves.
Figure 4:
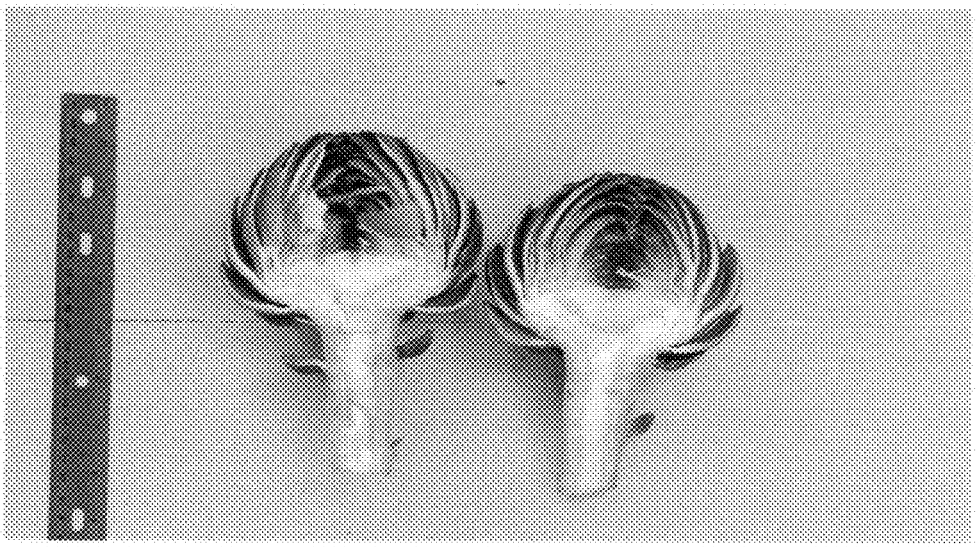
FIG. 4 depicts the cross-section of a harvested immature flower bud illustrating the inside bracts and receptacle.
Figure 5:
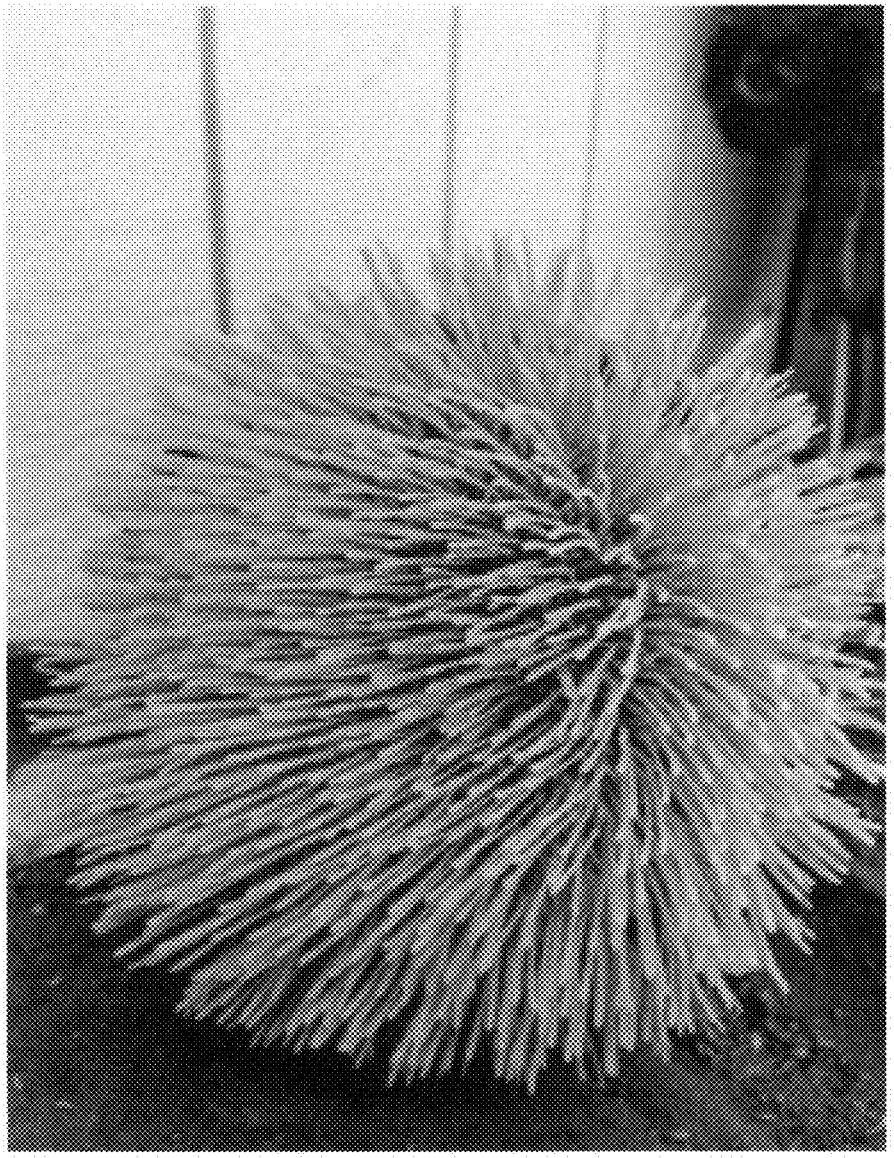
FIG. 5 depicts the top view of a mature inflorescence.
Figure 6:
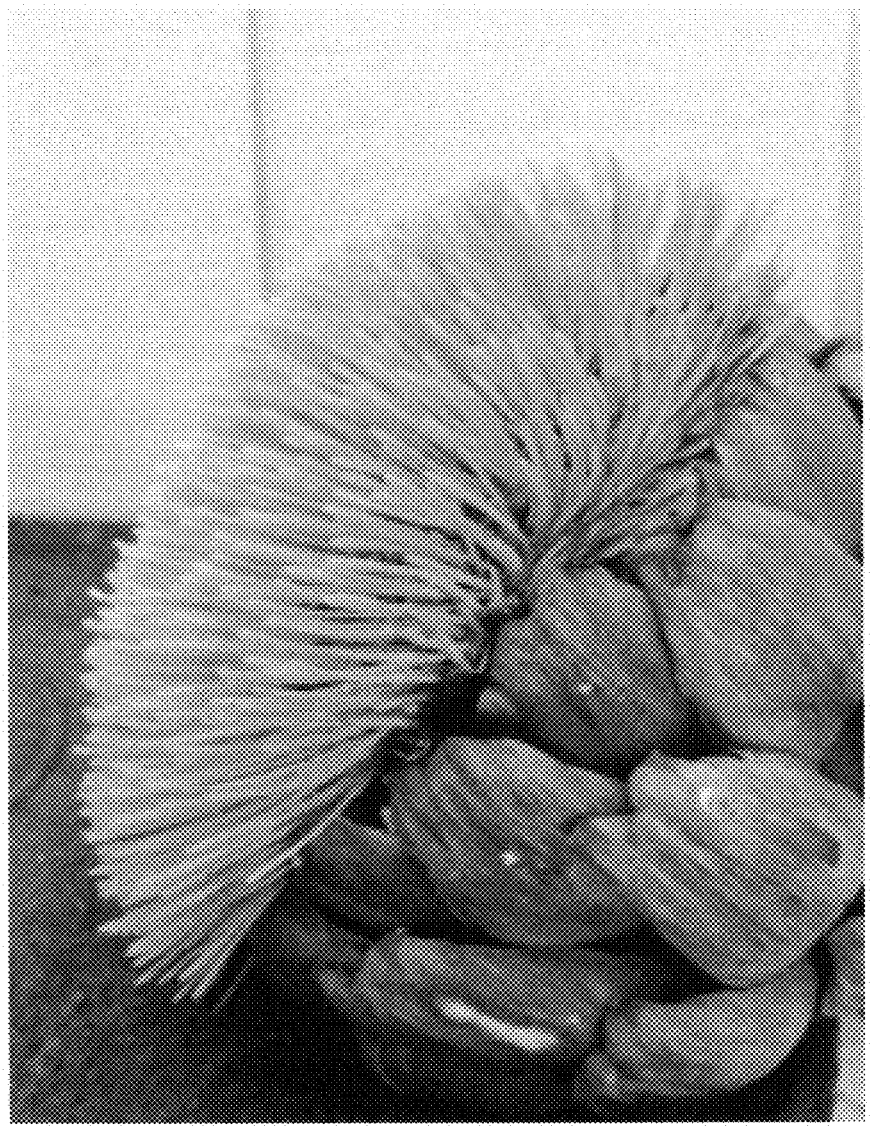
FIG. 6 depicts the side view of a mature inflorescence.

The drawings were made using conventional techniques and although immature flower bud and foliage color may appear different from actual color due to light reflectance, it is as accurate as possible by conventional photography.

DETAILED BOTANICAL DESCRIPTION

The following is a detailed botanical description of the new *Cynara* cultivar named 'SJ215'. Color determinations are in accordance with The 2001 Royal Horticultural Society Colour Chart of London, England, except where general color terms of ordinary dictionary significance are used. The following observations, measurements and values describe the new cultivar named 'SJ215' as grown in Lompoc, Calif. under conditions used in horticultural practice. Data was collected in April 2012 and June 2012 from field plants grown in rows where row spacing (bed centers) was 2 meters and individual plant spacing was 1.22 meters. Growing requirements are similar to the species.

Botanical classification: *CYNARA scolymus* 'SJ215'.

Family: Asteraceae (formerly Compositae).

Genus: *CYNARA*.

Species: *scolymus*.

Denomination: 'SJ215'.

Common name: Globe artichoke.

Commercial classification: Food crop.

Use: Production of edible vegetable delicacies.

Parentage: *Cynara scolymus* 'SJ215' was discovered as a natural somaclonal variant (sport) derived in a commercial crop in Lompoc, Calif. from the following parent:

*Parent*.—An individual *Cynara scolymus* 'BCL 9-11' (U.S. Plant Pat. No. 15,807).

Plant description:

*Months of harvest*.—Year round with greatest productivity March/April through September.

*Habit*.—Upright.

*Form*.—Full.

*Vigor*.—Vigorous.

*Type*.—Perennial herb.

*Height* (*range*).—119 cm. to 140 cm.

*Width* (*range*).—213 cm. to 222 cm.

*Root system*.—Thick and fibrous.

*Hardiness*.—USDA Zone 6.

*Asexual propagation method*.—Vegetative cuttings and tissue culture.

*Field crop time* (*range*).—5-6 months to produce a harvestable crop of edible immature flower buds from rooted cuttings.

*Disease resistance*.—None known to the inventor.

*Pest and disease susceptibility*.—Aphids, slugs, and leaf spot.

*Cultural requirements*.—Grow in full sun and well-draining alluvial soil, with moderate water.

Stem:

*Branching habit* (*range*).—Basal to caulescent.

*Stem density*.—Dense.

*Main stem diameter* (*average*).—8.7 cm.

*Main stem height* (*average*).—35 cm.

*Main stem surface*.—Ribbed.

*Main stem shape*.—Columnar.

*Side shoot quantity* (*range*).—3-5 per plant.

*Side shoot length* (*average*).—28 cm.

*Side shoot diameter* (*average*).—4 cm.

*Stem strength*.—Rigid.

*Stem color* (*range*).—138C to 138D (green group).

*Internode* (*range*).—4 cm. to 8.50 cm.

Foliage:

*Type*.—Evergreen.

*Arrangement*.—Alternate.

*Division*.—Simple.

*Margin* (*range*).—Entire to lobed.

*Quantity* (*range*).—14-18 per stem.

*Shape*.—Strap-like to pinnately lobed.

*Attachment*.—Decurrent.

*Abaxial surface leaf color* (*average*).—139D (green group).

*Adaxial surface leaf color* (*range*).—N138A to N138D (green group).
*Leaf length* (*range*).—45 cm.-90 cm.
*Leaf width* (*range*).—14 cm.-40 cm.
*Apex* (*range*).—Retuse to acute.
*Base*.—Truncate.
*Lobe quantity* (*average*).—10 per leaf.
*Lobe apex*.—Rounded.
*Lobe length* (*range*).—3 cm.-21 cm.
*Lobe width* (*range*).—3 cm.-7 cm.
*Venation pattern*.—Reticulate.
*Vein color* (*abaxial surface*).—150D (yellow-green group).
*Vein color* (*adaxial surface*).—150D (yellow-green group).
*Leaf surface* (*abaxial*).—Pubescent.
*Leaf surface* (*adaxial*).—Puberulent.
*Appearance* (*abaxial surface*).—Matte.
*Appearance* (*adaxial surface*).—Matte.
*Stipules*.—None observed.
*Fragrance*.—None observed.
*Angle of leaf to stem* (*average*).—45°.

Involucrum (immature flower bud):
*Shape* (*range*).—Globose to oblate.
*Apex* (*range*).—Broadly rounded to flattened obtuse.
*Base* (*range*).—Truncate to rounded.
*Central bud depth* (*average*).—13 cm.
*Central bud diameter* (*average*).—15 cm.
*Lateral bud depth* (*range*).—6 cm. to 12 cm.
*Lateral bud diameter* (*range*).—7 cm. to 13 cm.
*Form*.—Tightly compact.
*Texture*.—Firm.
*Surface*.—Glabrous.
*Quantity* (*range*).—16-35 per plant.
*Immature flower bud color* (*range*).—85A to 85D (pale violet group).
*Phyllary* (*involucral bract*).—Arrangement: Imbricate. Outer bract quantity (average): 19 per involucrum. Inner bract quantity (average): 25 per involucrum. Outer bract shape: Ovate. Inner bract shape: Oblong. Outer bract margin: Entire. Inner bract margin: Entire. Outer bract texture: Thick and fleshy. Inner bract texture: Thin and fleshy. Outer bract length (average): 6 cm. Outer bract width (average): 5.25 cm. Inner bract length (average): 5 cm. Inner bract width (average): 2 cm. Outer bract base width: 2.50 cm. Inner bract base width (average): 1.50 cm. Outer bract surface (ventral and dorsal): Glabrous. Inner bract surface (ventral and dorsal): Glabrous. Outer bract dorsal surface color (range): 85A-85D (pale-violet group). Outer bract ventral surface color (range): 138A to 138C (green group). Inner bract dorsal surface color (range): 86A-86D (violet group). Inner bract ventral surface color (combination): 158D (yellow-white group) and N77B (purple group). Outer bract appearance: Matte. Inner bract appearance: Irridescent. Outer bract apex (range): Retuse to emarginate. Outer bract base: Truncate. Inner bract apex: Acute. Inner bract base: Truncate. Spine (range): Diminutive to none observed.
*Receptacle shape*.—Concavo-convex.
*Receptacle diameter* (*average*).—4.50 cm.
*Receptacle depth* (*average*).—2 cm.
*Receptacle color*.—158A (yellow-white group).
*Receptacle texture*.—Firm.
*Pappus height* (*average*).—1.75 cm.
*Pappus diameter* (*average*).—3.50 cm.
*Pappus color*.—158D (yellow-white group).
*Bristle quantity*.—>500.
*Bristle shape*.—Filament.
*Bristle color*.—158D (yellow-white group).
*Bristle length* (*average*).—1.75 cm.
*Bristle width* (*average*).—<0.75 mm.
*Bristle texture*.—Sericeous.
*Peduncle shape*.—Columnar.
*Peduncle length* (*range*).—13 cm. to 26 cm.
*Peduncle diameter* (*range*).—1.50 cm. to 3 cm.
*Peduncle color range*.—138A to 138D (green group).
*Peduncle strength*.—Strong and rigid.
*Peduncle surface*.—Ribbed.
*Duration of cold storage* (*range*).—22-24 days.
*Cold storage temperature* (range).—1° to 2° Centigrade.
*Cold storage response*.—Negligible browning and softening at stem cut.
*Shelf life* (*range*).—22-28 days under mist.
*Weight* (*range*).—300-900 grams.

Mature inflorescence:
*Type*.—Capitula.
*Persistent or self-cleaning*.—Persistent.
*Fragrance*.—Mild fruity scent.
*Shape*.—Oblate.
*Weight* (*range*).—275-900 grams.
*Appearance*.—Thistle-like.
*Depth* (*average*).—11.30 cm.
*Diameter* (*average*).—12.50 cm.
*Bract*.—Arrangement: Imbricate. Outer bract quantity (average): 60 per inflorescence. Inner bract quantity (average): 110 per inflorescence. Outer bract shape: Ovate. Inner bract shape (range): Oblong. Margin (outer and inner bract): Entire. Outer bract texture: Leathery. Inner bract texture: Papyraceous. Outer bract height (average): 10.50 cm. Outer bract width (average): 5.50 cm. Inner bract height (average): 5 cm. Inner bract width (average): 2.50 cm. Outer bract surface (ventral and dorsal): Glabrous. Inner bract surface (ventral and dorsal): Glabrous. Outer bract color (dorsal surface): N80B to N80D (purple-violet group). Outer bract dorsal surface spotting (dorsal surface): 164A-164D (greyed-orange group). Outer bract color (ventral surface): N80B to N80D (purple-violet group). Inner bract color (dorsal surface): 165B (greyed-orange group). Inner bract color (ventral surface): 196C (greyed-green group). Outer bract appearance: Dull. Inner bract appearance: Irridescent. Outer bract apex: Emarginate. Outer bract base: Truncate. Outer bract base width (average): 2.50 cm. Inner bract apex: Acute. Inner bract base: Truncate. Inner bract base width (average): 1.25 cm. Receptacle diameter (average): 7 cm. Receptacle depth (average): 2 cm. Receptacle texture: Firm. Receptacle color: 159A (orange-white group). Disc floret quantity (average): 500+. Corolla dimensions: 1.50 cm. in depth and 3 mm. in diameter. Corolla color: 158A (yellow-white group). Pappus (modified calyx): Present. Pappus appearance: Irridescent. Pappus texture: Sericeous. Pappus color: 159A (orange-white group). Bristle quantity (average): 500+ per capitula. Bristle shape: Filamentous. Bristle color: 159A (orange-white group). Bristle length (average):

5.50 cm. Bristle texture: Sericeous silky. Peduncle shape: Columnar. Peduncle diameter (average): 0.80 cm. Peduncle length (average): 42 cm. Peduncle color: 144A (yellow-green group). Peduncle strength: Strong and rigid. Peduncle surface: Ribbed.

Reproductive organs:

*Stamen* (*per disc floret*).—5 in number.

*Stamen color.*—83C (violet group).

*Stamen length.*—1.50 cm.

*Pistil length*.—5 cm.

*Pistil color*.—83C (violet group).

*Stigma color* (*range*).—91A-91D (violet-blue group).

*Stigma height*.—2 cm.

*Ovary shape*.—Quadrangular.

*Ovary height*.—0.25 cm.

*Ovary color*.—159A (orange-white group).

*Ovary position*.—Inferior.

Seed: None observed to date.

The invention claimed is:

1. A new and distinct cultivar of artichoke plant named 'SJ215' as described and illustrated herein.

* * * * *